United States Patent [19]

Stalcup et al.

[11] Patent Number: 5,112,297
[45] Date of Patent: May 12, 1992

[54] TOPICAL ANESTHETIC APPLICATOR, DISPENSER SYSTEM, AND METHOD

[76] Inventors: Robert W. Stalcup, 21152 Peppertree La., Mission Viejo, Calif. 92691; Robert G. McCall, 7468 E. Raintree Crt., Scottsdale, Ariz. 95258

[21] Appl. No.: 488,658

[22] Filed: Mar. 5, 1990

Related U.S. Application Data

[63] Continuation-in-part of Ser. No. 400,281, Aug. 29, 1989, Pat. No. 5,016,651.

[51] Int. Cl.$^5$ .............................................. A61M 35/00
[52] U.S. Cl. ............................................ 604/1; 604/2; 604/290; 206/369; 206/63.5
[58] Field of Search .................. 206/363-366, 206/368-370, 438, 443, 63.5, 557-558, 562-563; 604/1-3, 290

[56] References Cited

U.S. PATENT DOCUMENTS

| | | | |
|---|---|---|---|
| 3,078,856 | 2/1963 | Bender et al. | 132/321 |
| 3,228,398 | 1/1966 | Leonard et al. | 604/1 |
| 4,194,290 | 3/1980 | Vallhonrat | 423/141 |
| 4,397,395 | 8/1983 | McKelvey | 206/369 X |
| 4,401,130 | 8/1983 | Halford et al. | 604/1 |
| 4,448,307 | 5/1984 | Roggenkamp | 206/369 |
| 4,466,973 | 8/1984 | Rennie | 424/267 |
| 4,664,291 | 5/1987 | Gunderson | 221/309 |
| 4,748,022 | 5/1988 | Busciglio | 424/195.1 |
| 4,795,421 | 1/1989 | Blasius, Jr. et al. | 604/1 |
| 4,887,994 | 12/1989 | Bedford | 604/2 X |
| 4,978,510 | 12/1990 | Smith | 422/310 |
| 4,989,730 | 2/1991 | Lemoine | 206/362 |

*Primary Examiner*—C. Fred Rosenbaum
*Assistant Examiner*—C. Maglione
*Attorney, Agent, or Firm*—Knobbe, Martens, Olson & Bear

[57] ABSTRACT

An improved applicator for applying a topical anesthetic to a patient's mucosal tissue is disclosed, and includes a sponge-like dispenser member characterized by a relatively large surface area. The dispenser member is attached to an elongated handle. A predetermined quantity of the topical anesthetic is preapplied to the applicator member. A number of the applicators are stored in a refillable dispenser apparatus, wherein a refill dispenser housing defines a number of applicator wells, each for receiving one of the applicators. The handles of the applicators can be color-coded to indicate the flavor of the topical anesthetic which has been preapplied to the applicator.

10 Claims, 2 Drawing Sheets

TOPICAL ANESTHETIC APPLICATOR, DISPENSER SYSTEM, AND METHOD

This is a continuation-in-part of parent patent application Ser. No. 400,281, filed Aug. 29, 1989, by inventors Robert W. Stalcup and Robert G. McCall, and entitled TOPICAL ANESTHETIC APPLICATOR AND DISPENSER SYSTEM now U.S. Pat. No. 5,016,651.

BACKGROUND OF THE INVENTION

The present invention relates to applicators for applying topical anesthetics to a patient's mucosal tissue, such as the patient's mouth, for locally anesthetizing the patient's mucosal tissue.

Topical anesthetics are in common use today to locally anesthetize an area of a patient's mouth prior to carrying out a particular dental procedure, such as a blockage injection. Commonly used topical anesthetics include derivatives of benzocaine (ethyl aminobenzoate) or zylocaine (lidocaine) in a non-irritating water soluble base composed of polymerized polyethylene glycols.

The anesthetic is typically supplied in small jars containing a quantity of anesthetic sufficient for a number of dental procedures. Conventionally, the dentist applies the topical anesthetic by first dipping a cotton swab into the anesthetic in the jar to apply a quantity of the anesthetic to the swab, with the swab then used to transfer the anesthetic to the localized area of the patient's mouth. The same jar is typically a "community" jar used for a number of procedures for different patients. Alternatively, small multiple dose syringes filled with the anesthetic have been used to dispense the anesthetic to cotton rolls and swabs.

The conventional system for applying topical anesthetic suffers several disadvantages. The dentist or dental assistant must individually precoat the swab by dipping it into the community jar. This is time consuming, and it is difficult to apply a precise or desired quantity of the topical anesthetic. Sometimes too much anesthetic is applied to the cotton swab and the anesthetic can drip off, e.g., onto the patient's tongue or throat. The dripping can cause discomfort to the patient or anesthetize the wrong area. The use of a community jar may lead to unsanitary conditions if the jar is not sealed after each use. A cotton swab has a relatively small surface area, and therefore a second application may be required for some procedures.

SUMMARY OF THE INVENTION

It is therefore an object of the invention to provide an improved, single-use applicator for topical anesthetics to which has been preapplied a predetermined quantity of the topical anesthetic, and providing an increased surface area of contact with the mucosal tissue, enhancing the effect of the anesthetic.

It is a further object of the invention to provide a dispenser system for the improved applicator to provide precoated applicators in a sanitary and convenient manner.

These and other objects and advantages are achieved by a topical anesthetic applicator and dispenser system in accordance with the invention. The applicator comprises a sponge-like applicator member characterized by a relatively large surface area and high absorption of the topical anesthetic, and an elongated handle affixed to the sponge-like applicator member. A predetermined amount of topical anesthetic is preapplied to the applicator member in accordance with the invention. The relatively large surface area of the applicator member enhances the effect of the anesthetic to the mucosal tissue.

The applicators are preferably dispensed from a dispenser apparatus comprising a refill dispenser defining a plurality of applicator wells, each for receiving one of the applicator members. The refill dispenser housing is removably received within a dispenser base structure which includes a lid which can be raised or lowered, the lid covering the wells when in the lowered position. Preferably, the refill dispenser includes a large number of wells, thereby holding a large number of applicators. The handles of the applicators may be color-coded to indicate the flavor of the anesthetic.

BRIEF DESCRIPTION OF THE DRAWINGS

These and other features and advantages of the present invention will become more apparent from the following detailed description of an exemplary embodiment thereof, as illustrated in the accompanying drawings, in which.

DETAILED DESCRIPTION OF THE PREFERRED EMBODIMENT

Figure 1:
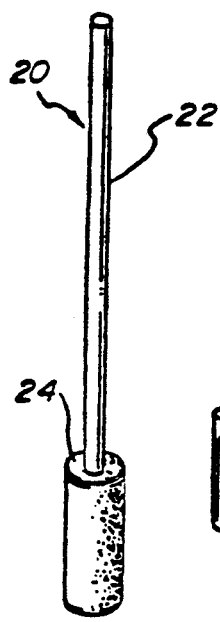
FIG. 1 is a perspective view of an improved applicator for topical anesthetics in accordance with the invention.

Referring now to FIG. 1, a preferred embodiment of the applicator 20 for topical anesthetics is illustrated. The preferred embodiment is discussed in the context of dental applications, although it is to be understood that the invention has utility generally to apply topical anesthetics to mucosal tissue. Thus, other medical applications exist to apply anesthetic to such exemplary areas as the mucosal tissue in the nose.

The applicator 20 comprises an elongated handle 22 covered at one end thereof by an applicator member 24 characterized by an extended surface area. Preferably, the member 24 comprises a material such as a soft sponge-like material such as an open celled foam rubber or like material. One shape of the applicator member 24 suitable for this purpose is a cylindrical shape as shown in FIG. 1. Other shapes and configurations can also be employed. The cylindrical configuration is well suited to dental applications. This configuration facilitates the application of positive pressure of the applicator member 24 against the mucosal tissue, which is particularly useful to anesthetize a local area in preparation for a block injection. Obviously, the material chosen for member 24 must be non-toxic, and is preferably absorbent of the particular topical anesthetic to be applied.

For dental applications, the overall length of the applicator 20 is preferably in the range of 3 to 4 inches with a handle diameter of about ⅛ inch; an overall length of about 3½ inches is particularly advantageous for dental applications. The member 24 preferably has an outer diameter of ¼ to ½ inch with a cylinder length in the range of ½ to ¾ inch. Handles and applicator members of other dimensions may also be used.

The soft sponge applicator member 24 serves to carry the topical anesthetic, and has the advantage of increasing the surface area of contact with the patient's mucosal tissue, as compared to the surface area of a conventional cotton swab, thereby enhancing the effect of the anesthetic. When an applicator member 24 is employed having the exemplary dimensions described above, it may be used to apply the anesthetic to a tissue surface area adjacent two or three teeth. In contrast, the conventional cotton swab typically covers only a surface area adjacent a single tooth, requiring two or more swab applications for some procedures. When the applicator 20 is used to locally anesthetize an area adjacent the upper teeth, for example, the diameter of the applicator 20 is sufficient to wedge the applicator 20 between the patient's cheek and jaw. Thus, the applicator remains in contact with the mucosal tissue without being held in place by the dentist or technician. When cotton swabs have been used for this purpose, the swabs have a tendency to fall out due to the relatively small diameter of the cotton swab.

In accordance with the invention, a predetermined amount of the topical anesthetic is applied to the applicator member 24. This may be done, e.g., by dipping the dispenser in a bath of the anesthetic. Other techniques may also be used to apply the anesthetic. Typically, the anesthetic may be in a substantially liquid form when applied to the applicator member 24, and thereafter solidifies into a gel-like form on the applicator. The sponge-like material of member 24 absorbs the anesthetic at least into the cells at the surface of member 24. The "predetermined quantity" of the anesthetic applied to the applicator 20 will be determined by the absorptiveness of the sponge-like material and the viscosity of the anesthetic. The quantity may not be precisely determined, and it is not critical for dental applications that the quantity be precisely measured. It is desired that the applicators have about the same quantity of anesthetic applied to member 24, that enough anesthetic be applied to effectively treat mucosal tissue coming into contact with the surface area of member 24, and yet that an excessive amount not be applied such that the anesthetic drips from the applicator 20 when dispensed for use.

After a particular applicator 20 has been used once, it is discarded. This one-time use without a community jar tends to increase patient confidence in the anesthetic procedure.

Figure 2:
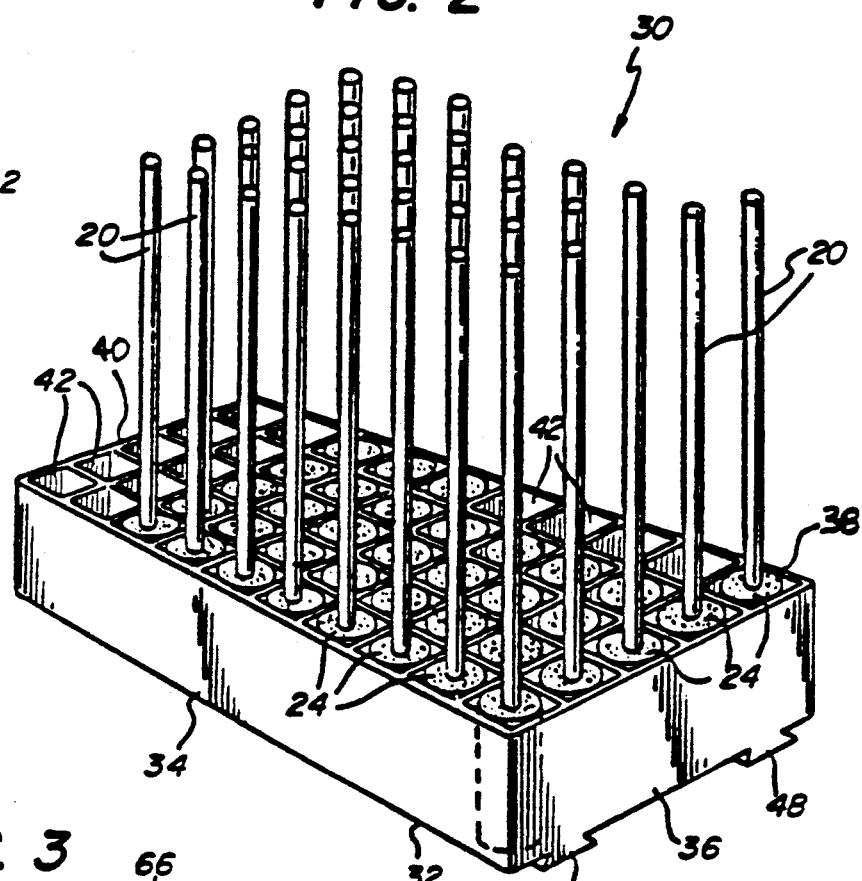
FIG. 2 is a perspective view of an applicator dispenser for holding a plurality of dispensers as shown in FIG. 1.

Referring now to FIG. 2, a perspective view of a refill dispenser 30 is disclosed for the applicators 20 illustrated in FIG. 1. The dispenser 30 comprises a boxlike structure having a bottom plate 32 and four upright walls 34, 36, 38 and 40. The interior of the dispenser 30 is divided into a plurality of partitioned wells 42, each for receiving an applicator 20. The applicators 20 are preferably disposed with the applicator members 24 inserted in the wells 42 so that the handles 22 protrude for convenient access by the dentist. Preferably, the refill dispenser 30 includes at least fifty wells 42.

The dispenser 30 may be fabricated from plastic or other similar material. Protruding tracks 46 and 48 having a wedge-shaped cross-sectional configuration are formed in the bottom surface 32 of the dispenser 30 and removably secure the dispenser 30 to the base member 50 shown in FIG. 3.

Figure 3:
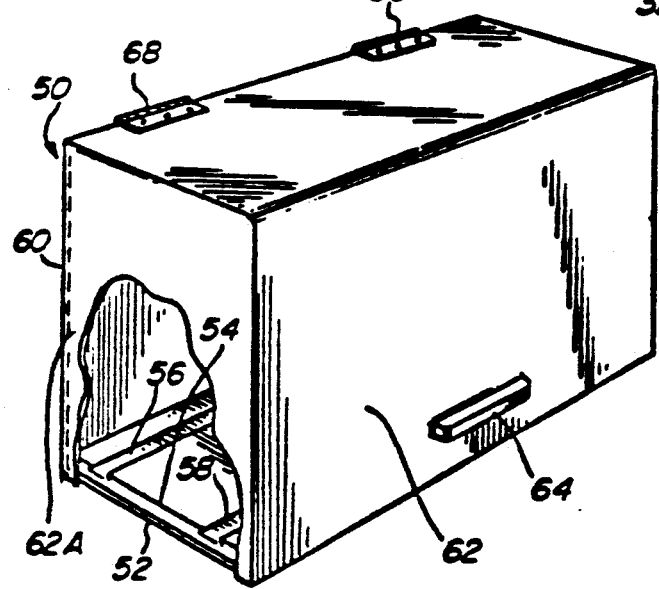
FIG. 3 is a perspective view of a dispenser base for receiving the dispenser of FIG. 2 to supply the applicators in a sanitary dispenser system.

FIG. 3 illustrates the base structure 50 used to support the dispenser 30 and provide a closable top. The base structure 50 comprises a weighted base member 52 into which is fitted a plate 54 having defined therein base grooves 56 and 58 which mate with the tracks 46 and 48 formed in the bottom of the dispenser 30. The plate 54 supports the refill dispenser 30. The base structure 50 further comprises a back upright wall 60 and a curved top cover member 62, which is connected to the back wall 60 by hinges 66 and 68. The top member 62 further comprises side wall elements 62A on either side of the curved top 62 to enclose the sides of the structure 50. A handle 64 is provided to facilitate raising and lowering the top 62. The base structure 50 and the refill dispenser 30 cooperate to define a sanitary enclosure for the applicators 20 which is conveniently accessible by the dentist.

Figure 4:
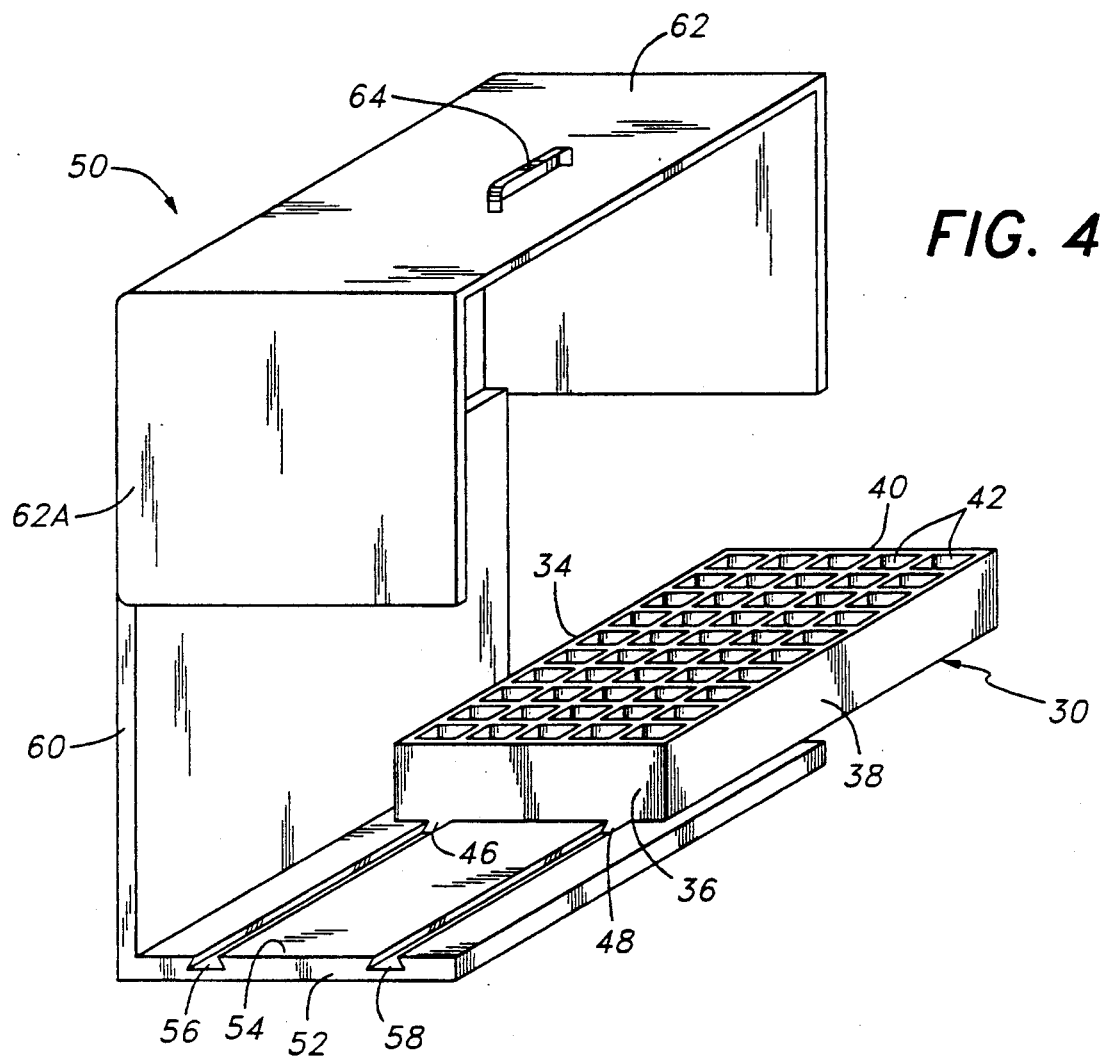
FIG. 4 is a perspective view of the dispenser base of FIG. 3 with the top raised and an empty dispenser partially removed from the base.

As can be seen in FIG. 4, the curved top cover member 62 and side wall elements 62A rotate about the hinges 66 and 68 (not shown), which connect them to the base upright wall 60. By lifting the handle 64, the top 62 can be raised to allow clearance for endwise insertion of the dispenser 30 into the base structure 50. The dispenser 30 can be slipped into the base structure 50 by raising the cover 62, aligning the tracks 46 and 48 of the dispenser 30 with the corresponding track grooves 56 and 58 of the base plate 54, and sliding the dispenser 30 into the base structure 50. Upon depletion of the dispenser 30, it can be removed as shown in FIG. 4 and replaced with a full dispenser.

It is contemplated that the dispenser 30 will be marketed with all wells 42 filled with the applicators 20 as described above with respect to FIG. 1. The filled dispenser 30 can be shipped in sealed packaging, and used to refill the base structure 50. Thus, no handling of the individual applicators need be made during shipping or installation of the dispenser 30 in the base structure 50. Alternatively, the individual applicators 20 may be sealed before being placed in the dispenser 30.

It is known to use anesthetics having different taste flavors, e.g., strawberry, butterscotch and the like. In accordance with another aspect of the invention, the handles 22 can be color-coded to indicate the particular flavor of the preapplied anesthetic. The dentist can then ask the patient which flavor is desired, and immediately pick up an applicator preapplied with the anesthetic of that flavor simply by knowing the particular color associated with the selected flavor. For convenience, each row of applicators 20 in the dispenser 30 may hold applicators of a particular flavor of anesthetic.

Figure 5:
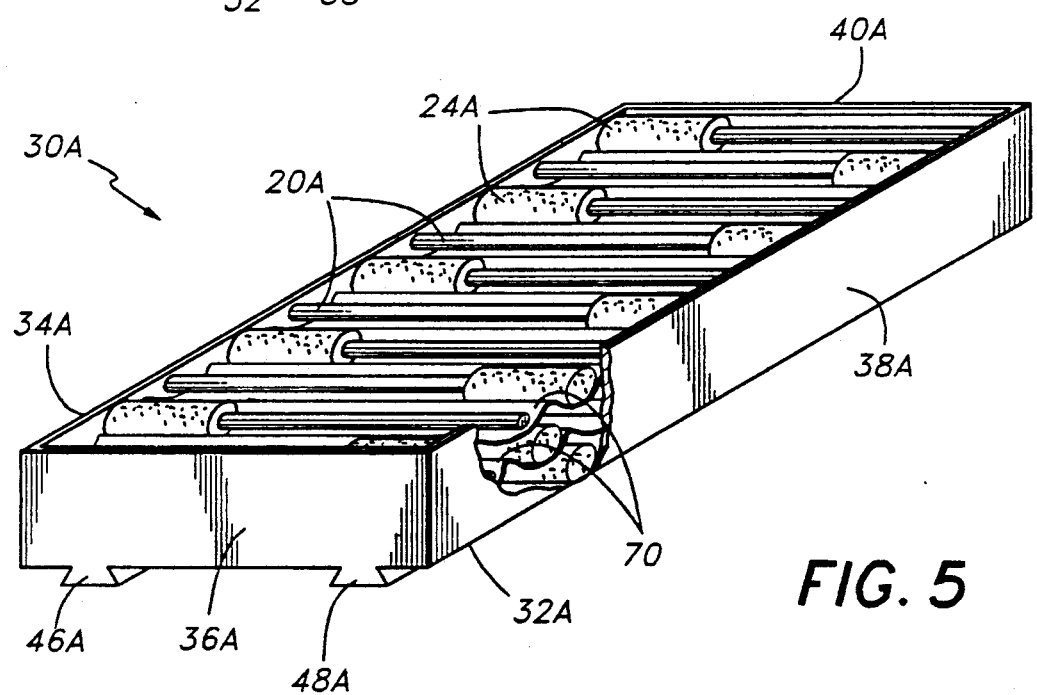
FIG. 5 is a perspective view of an alternate embodiment of the applicator dispenser.

FIG. 5 shows an alternative embodiment of the topical anesthetic dispenser 30 of the present invention. In the alternative embodiment, the dispenser 30A does not have the wells 42 of the preferred embodiment, but instead contemplates stacking the applicators 20A in alternating fashion in layers as shown. The bottom plate 32A, walls 34A, 36A, 38A and 40A, and tracks 46A and 48A of the dispenser 30A may be identical to that of the preferred embodiment shown in FIG. 2. Likewise, the applicators 20A, handles 22A and applicator members 24A of the alternate embodiment shown in FIG. 5 may be identical to those of the preferred embodiment. The primary difference is that, instead of the wells 42 of the preferred embodiment, the applicators are separated by the spacer strips 70. The spacer strips may take the from of flat strips or, as shown in FIG. 5, may be indented to facilitate horizontal spacing as well as vertical stacking of the applicators 20A.

The alternate embodiment shown in FIG. 5 may be preferred where minimum height is a desired objective. As can be seen by comparing FIG. 5 with FIG. 2, the dispenser of the alternate embodiment may be made considerably shorter than that of the preferred embodiment. One of ordinary skill will appreciate other configurations of both dispenser and base structures that will work equally as well as the two embodiments disclosed herein.

It is understood that the above-described embodiments are merely illustrative of the possible specific embodiments which may represent principles of the present invention. Other arrangements may readily be devised in accordance with these principles by those skilled in the art without departing from the scope of the invention.

What is claimed is:

1. An applicator dispenser system for topical anesthetic applicators, comprising:
   a plurality of applicators having:
      a soft, sponge-like applicator member characterized by a relatively high absorptivity and having a substantially cylindrical configuration with a diameter in the range of ¼ to ½ inch and a length sufficient to allow coverage of mucosal tissue adjacent at least two adult human teeth;
      a predetermined amount of topical anesthetic suitable for application to human oral mucosal tissue preapplied to said applicator member; and
      an elongated handle affixed to said applicator member; and
   an applicator dispenser apparatus for storing said applicators and allowing selective removal thereof for use, said applicator dispenser apparatus having a refill dispenser housing structure comprising means for defining a plurality of wells for receiving said applicators.

2. The applicator dispenser system of claim 1, wherein said dispenser apparatus comprises a dispenser tray for removably receiving and supporting said applicators.

3. The applicator dispenser system of claim 2, wherein said dispenser apparatus further comprises a base structure for removably receiving said dispenser tray.

4. The applicator dispenser system of claim 3, wherein said dispenser tray has a bottom surface having elongated tracks protruding therefrom, and wherein said base structure has a surface having defined therein grooves for receiving therein the elongated tracks protruding from the dispenser tray.

5. An applicator dispenser system for topical anesthetic applicators, comprising:
   a dispenser;
   a plurality of applicators removably received in said dispenser having:
      an elongated handle;
      a soft, sponge like applicator member having a diameter in the range of ¼ to ½ inch and a length in the range of ½ to ¾ inch mounted on said elongated handle; and
      a predetermined amount of topical anesthetic suitable for application to oral mucosal tissue preapplied to said applicator member; and
   a base for selectively receiving said dispenser said base having a cover which is selectively openable to allow insertion and removal of said applicators.

6. The system of claim 5, wherein said selectively openable cover also allows insertion and removal of said dispenser.

7. The system of claim 5, wherein said dispenser has a plurality of wells for receiving said applicators.

8. The system of claim 5, wherein said applicators are received in said dispenser in layers.

9. An applicator dispenser system for topical anesthetic applicators, comprising:
   a plurality of applicators having:
      a soft, sponge-like applicator member characterized by a relatively high absorptivity and having a substantially cylindrical configuration with a diameter in the range of ¼ to ½ inch and a length sufficient to allow coverage of mucosal tissue adjacent at least two adult human teeth;
      a predetermined amount of topical anesthetic suitable for application to human oral mucosal tissue preapplied to said applicator member; and
      an elongated handle affixed to said applicator member; and an applicator dispenser apparatus having:
      a dispenser tray for removably receiving therein said applicators; and
      a base structure for receiving and supporting said dispenser tray having securing means for releasably securing said dispenser tray to said base structure and a selectively openable cover to allow insertion and removal of said dispenser tray, removal of said applicators for use and protection of said applicators in said dispenser tray.

10. A method of applying topical anesthetic to a human patient's oral mucosal tissue in a selected area adjacent at least two teeth, comprising the steps of:
   providing an applicator having:
      a soft, sponge-like applicator member configured to allow insertion between the patient's cheek and jaw and retention therebetween;
      a predetermined amount of topical anesthetic suitable for application to oral mucosal tissue preapplied to said applicator member; and
      an elongated handle affixed to said applicator member, said applicator member covering one end of said handle;
   separating said patient's cheek and jaw;
   grasping said applicator by said handle;
   inserting said applicator member between said patient's cheek and jaw adjacent the selected area;
   releasing the patient's cheek, thereby allowing said cheek to urge said applicator member into contact with the oral mucosal tissue in the selected area, whereby said urging maintains contact between said anesthetic and said oral mucosal tissue so as to enhance the effect of said anesthetic on the oral mucosal tissue in the selected area.

* * * * *